(12) United States Patent
Zarkh et al.

(10) Patent No.: US 7,587,074 B2
(45) Date of Patent: Sep. 8, 2009

(54) METHOD AND SYSTEM FOR IDENTIFYING OPTIMAL IMAGE WITHIN A SERIES OF IMAGES THAT DEPICT A MOVING ORGAN

(75) Inventors: Michael Zarkh, Giv'at Shmuel (IL); Moshe Klaiman, Gedera (IL)

(73) Assignee: Paieon Inc., New York, NY (US)

( * ) Notice: Subject to any disclaimer, the term of this patent is extended or adjusted under 35 U.S.C. 154(b) by 504 days.

(21) Appl. No.: 10/565,224

(22) PCT Filed: Jul. 14, 2004

(86) PCT No.: PCT/IL2004/000632

§ 371 (c)(1),
(2), (4) Date: Jan. 20, 2006

(87) PCT Pub. No.: WO2005/008583

PCT Pub. Date: Jan. 27, 2005

(65) Prior Publication Data

US 2006/0188135 A1    Aug. 24, 2006

(51) Int. Cl.
*G06K 9/00* (2006.01)
(52) U.S. Cl. .................. 382/128; 382/107
(58) Field of Classification Search ......... 382/128–132; 600/420–427, 431; 378/69; 128/922
See application file for complete search history.

(56) References Cited

U.S. PATENT DOCUMENTS

| | | |
|---|---|---|
| 4,263,916 A | 4/1981 | Brooks et al. |
| 4,889,128 A | 12/1989 | Millar |
| 5,175,773 A | 12/1992 | Bouliou et al. |
| 5,203,777 A | 4/1993 | Leeq |
| 5,446,800 A | 8/1995 | Briggs et al. |
| 5,583,902 A | 12/1996 | Bae |
| 5,699,799 A | 12/1997 | Xu et al. |
| 5,718,724 A | 2/1998 | Goicoechea et al. |
| 5,729,129 A | 3/1998 | Acker |

(Continued)

FOREIGN PATENT DOCUMENTS

DE    100 47 314    4/2001

(Continued)

OTHER PUBLICATIONS

Rita Noumeir, Guy E. Mailloux, Raymond Lemieux, Detection of Motion during Tomographic Acquisition by an Optical Flow Algorithm, Computers and Biomedical Researchvol. 29, Issue 1, Feb. 1996, pp. 1-15.*

(Continued)

*Primary Examiner*—Vikkram Bali
*Assistant Examiner*—Andrae S Allison
(74) *Attorney, Agent, or Firm*—Ladas & Parry LLP

(57) ABSTRACT

A method and system for quantifying a cyclic motion within a series of images depicting a moving object subject to composite motion containing a cyclic component and a non-cyclic component of lower frequency than the cyclic component. Composite motion is computed as well as the non-cyclic component as the integral of motion over a motion cycle. The non-cyclic component is subtracted from the composite motion so as to obtain the cyclic component

28 Claims, 3 Drawing Sheets

U.S. PATENT DOCUMENTS

| | | | |
|---|---|---|---|
| 5,732,707 | A | 3/1998 | Widder et al. |
| 5,734,384 | A | 3/1998 | Yanof |
| 5,840,025 | A | 11/1998 | Ben-Haim |
| 5,912,945 | A | 6/1999 | Da Silva et al. |
| 6,027,460 | A | 2/2000 | Shturman |
| 6,047,080 | A | 4/2000 | Chen et al. |
| 6,094,591 | A | 7/2000 | Foltz et al. |
| 6,144,875 | A * | 11/2000 | Schweikard et al. ........ 600/427 |
| 6,152,878 | A * | 11/2000 | Nachtomy et al. .......... 600/467 |
| 6,167,296 | A | 12/2000 | Shahidi |
| 6,190,353 | B1 | 2/2001 | Makower et al. |
| 6,195,577 | B1 | 2/2001 | Truwit et al. |
| 6,233,476 | B1 | 5/2001 | Strommer et al. |
| 6,246,898 | B1 | 6/2001 | Vesely et al. |
| 6,249,695 | B1 | 6/2001 | Damadian |
| 6,290,673 | B1 | 9/2001 | Shanley |
| 6,301,498 | B1 | 10/2001 | Greenberg et al. |
| 6,314,312 | B1 * | 11/2001 | Wessels et al. .............. 600/427 |
| 6,332,034 | B1 | 12/2001 | Makram-Ebeid et al. |
| 6,334,864 | B1 | 1/2002 | Amplatz et al. |
| 6,351,513 | B1 | 2/2002 | Bani-Hashemi et al. |
| 6,352,508 | B1 * | 3/2002 | Pang et al. .................. 600/443 |
| 6,381,350 | B1 | 4/2002 | Klingensmith et al. |
| 6,385,332 | B1 | 5/2002 | Zahalka et al. |
| 6,402,693 | B1 * | 6/2002 | Emery ......................... 600/443 |
| 6,463,309 | B1 | 10/2002 | Ilia |
| 6,501,848 | B1 | 12/2002 | Carroll et al. |
| 6,501,981 | B1 * | 12/2002 | Schweikard et al. ........ 600/427 |
| 6,503,203 | B1 | 1/2003 | Rafter et al. |
| 6,505,064 | B1 | 1/2003 | Liu et al. |
| 6,544,230 | B1 | 4/2003 | Flaherty et al. |
| 6,709,444 | B1 | 3/2004 | Makower |
| 6,748,259 | B1 | 6/2004 | Benaron et al. |
| 6,990,368 | B2 | 1/2006 | Simon et al. |
| 7,024,025 | B2 * | 4/2006 | Sathyanarayana ........... 382/128 |
| 7,027,650 | B2 * | 4/2006 | Williame et al. ............ 382/215 |
| 7,074,188 | B2 * | 7/2006 | Nair et al. ................... 600/443 |
| 7,092,571 | B2 * | 8/2006 | Hsieh .......................... 382/209 |
| 7,092,572 | B2 * | 8/2006 | Huang et al. ................ 382/218 |
| 7,215,802 | B2 * | 5/2007 | Klingensmith et al. ...... 382/128 |
| 7,359,535 | B2 * | 4/2008 | Salla et al. .................. 382/128 |
| 7,359,554 | B2 * | 4/2008 | Klingensmith et al. ...... 382/199 |
| 7,367,953 | B2 * | 5/2008 | Salla et al. .................. 600/508 |
| 7,397,935 | B2 * | 7/2008 | Kimmel et al. ............. 382/128 |
| 2002/0057825 | A1 | 5/2002 | Evron et al. |
| 2003/0032886 | A1 | 2/2003 | Dgany et al. |
| 2004/0102697 | A1 | 5/2004 | Evron |
| 2004/0136491 | A1 | 7/2004 | Iatrou et al. |
| 2005/0113686 | A1 | 5/2005 | Peckham |

FOREIGN PATENT DOCUMENTS

| | | |
|---|---|---|
| EP | 0 885 594 | 12/1998 |
| EP | 0 885 594 A2 | 12/1998 |
| EP | 1 005 835 | 6/2000 |
| SU | 2119765 | 10/1988 |
| WO | WO 96 25881 | 8/1996 |
| WO | WO 99 13432 | 3/1999 |
| WO | WO 01 58359 | 8/2001 |
| WO | WO 01/85030 | 11/2001 |
| WO | WO 02/36013 | 5/2002 |
| WO | WO 03/096884 | 11/2003 |
| WO | WO 2005/008583 | 1/2005 |
| WO | WO 2005/020148 | 3/2005 |
| WO | WO 2005/031635 | 4/2005 |
| WO | WO 2006/033113 | 3/2006 |
| WO | WO 2006/061815 | 6/2006 |

OTHER PUBLICATIONS

Nelson, Thomas R., et al., "Three-Dimensional Ultrasound Imaging," *Ultrasound in Medicine and Biology,* New York, NY, vol. 24, No. 9, pp. 1243-1270 (Dec. 1998).

Ratib, Osman, "Quantitative Analysis of Cardiac Function," *Handbook of Medical Imaging—Processing and Analysis,* Ed. I. Bankman, Academic Press, pp. 359-374 (2000).

Penney G P et al "A Comparison of Similarity Measures for Use in 2-D-3-D Medical Image Registration" IEEE Transactions on Medical Imaging, IEEE Service Center, Piscataway, NJ, US, vol. 17 ,No. 4. pp. 586-595, Aug. 1998.

Russakoff D B et al "Intensity-based 2D-3D spine image registration incorporating a single fiducial marker" Academic Radiology, Reston, VA, US, vol. 12, No. 1. pp. 37-50, Jan. 2005.

Srihari R et al "Image background search: combining object detection techniques with content-based image retrieval (CBIR) systems" Content-Based Access of Image and Video Libraries, 1999. (CBAIVL '99). Proceedings. IEEE Workshop on Fort Collins, CO, US, Los Alamitos, CA, USA,IEEE Comput. Soc, US, 1999, pp. 97-101.

Eiho S et al "Preoperative and intraoperative image processing for assisting endovascular stent grafting" Informatics Research for Development of Knowledge Society Infrastructure, 2004.ICKS 2004. International Conference on Kyoto, Japan Mar. 1-2, 2004, Piscataway, NJ, USA,IEEE. pp. 81-88.

Close R A et al "Accuracy Assessment of Layer Decomposition Using Simulated Angiographic Image Sequences" IEEE Transactions on Medical Imaging, IEEE Service Cente, Piscataway, NJ, US, vol. 20, No. 10. pp. 990-998, Oct. 2001.

Nelson T R et al "Three-dimensional ultrasound imaging" Ultrasound in Medicine and Biology, NewYork, NY, US, vol. 24, No. 9. pp. 1243-1270, Mar. 1998.

Bankman I "Handbook of Medical Imaging Progressing and Analysis" 2000, Academic Press, San Diego, London. pp. 359-374.

Garreau M et al " A knowledge-based approach for 3-D reconstruction and labeling of vascular networks from biplane Angiographic projections" IEEE transactions on medical imaging, US, IEEE inc. vol. 10 , No. 2, Jun. 1991.

* cited by examiner

| From point | To point | dX | dY | X | Y |
|---|---|---|---|---|---|
| 0 | 1 | 1 | 1 | 1 | 1 |
| 1 | 2 | 1 | 0 | 2 | 1 |
| 2 | 3 | 1 | 0 | 3 | 1 |
| 3 | 4 | 1 | -1 | 4 | 0 |
| 4 | 5 | 0 | -1 | 4 | -1 |
| 5 | 6 | 0 | -1 | 4 | -2 |
| 6 | 7 | -1 | -1 | 3 | -3 |
| 7 | 8 | -1 | 0 | 2 | -3 |
| 8 | 9 | -1 | 0 | 1 | -3 |
| 9 | 10 | -1 | -1 | 0 | -4 |
| 10 | 11 | -1 | 0 | -1 | -4 |
| 11 | 12 | 0 | 1 | -1 | -3 |
| 12 | 13 | 0 | 1 | -1 | -2 |
| 13 | 14 | 1 | 1 | 0 | -1 |
| 14 | 0 | 0 | 1 | 0 | 0 |

METHOD AND SYSTEM FOR IDENTIFYING OPTIMAL IMAGE WITHIN A SERIES OF IMAGES THAT DEPICT A MOVING ORGAN

FIELD OF THE INVENTION

This invention relates to medical image processing devices.

BACKGROUND OF THE INVENTION

Medical imaging devices are often used to image moving organs. Cardiac image processing devices, in particular, are always used to image moving organs, either the heart (via ultrasound imaging for example), or the coronaries (via angiography for example). Many of these imaging processing devices are used to quantify the motion either as an indication by itself or as part of an image-processing algorithm.

An image processing device for Left Ventricle Analysis is used to evaluate Ejection Fraction, which is the percentage of the blood pumped out during each heartbeat. Left Ventricle Analysis involves computing the Left Ventricle volume from an angiogram (taken from a cine-angio sequence of images). The Left Ventricle volume is computed once for the heart in its systolic phase and once for the heart in its diastolic phase. Ejection Fraction is estimated from the ratio of these volumes. Identifying the systolic and diastolic images is part of the LVA procedure.

Myocardium thickness and Heart Wall Motion are evaluated from Ultrasound Images to indicate heart failure conditions. Both procedures, again, involve the identification of systolic and diastolic instances. Furthermore, quantifying the object's motion could be directly used for Wall Motion evaluation.

Intra-Vascular Ultrasound (IVUS) is a method of evaluating and analyzing coronary defects by means of inserting an intra-vascular ultrasound device and imaging the vessel. IVUS measurements include measurements of the luminal vessel area. Estimation of the luminal area very much depends on the heart phase and results vary for different images depicting different stages within the cardiac cycle. Again, it is useful to identify the diastolic—or the minimal movement instance—in order to perform measurements on the optimal image.

CT, MRI and PET are also used to image the heart as well as the coronary arteries. These methods use ECG triggering that synchronize image acquisition to ECG events (for example end diastole) in order to decrease motion artifacts that decrease image resolution and image quality, thus impairing the image result and consequently clinical assessments.

In the field of medical imaging, angiography is a gold standard for cardio-vascular diagnostics. Conventional (2D) angiography, produced by C-Arm X-ray equipment, applied during a catheterization procedure, provides a most accurate modality for evaluating vessel disease. Quantitative Coronary analysis is often applied to measure vessel disease. Analysis is applied to a certain angiogram to measure vessel dimensions; the results are different, when derived from different angiograms, depicting the vessel in different instances of the heart cycle; QCA procedure recommends the use of the end-diastole image.

Three-Dimensional reconstruction of coronary vessels is also a method of evaluating vessel disease from a procedure of conventional angiography. While it is well known and widely covered in the literature that 2D angiography has some inherent drawbacks, mainly presenting and measuring projected objects, which result in inaccurate measurements, methods are available for performing three-dimensional reconstruction of the arteries from the series of the two-dimensional images obtained. In order to reconstruct a three-dimensional image of the arteries, it is necessary to obtain at least two two-dimensional images of the arteries in the same phase of the heartbeat, for example at diastole. Therefore, image acquisition is usually synchronized to an E.C.G signal. This procedure involves simultaneous recordings of the video signal from the X-ray camera and the patient's E.C.G signal. This procedure of ECG gating suffers from many drawbacks. For example, the ECG signal, in many cases, is hard to correlate to a desired state of the coronaries. Furthermore, when reviewing recorded angiographic films, often the E.C.G signal is unavailable.

There are many additional cardiac and other medical procedures and measurements that involve identifying instances within the object's movement cycle and also involve quantifying this movement.

Thus, it is desirable to quantify the organ movements. It is desirable to identify instances within the movement cycle. It is also evident that imaging a moving organ poses great difficulties for all modalities, impairing quantitative results and clinical assessment.

SUMMARY OF THE INVENTION

It is an object of the invention to provide a method and system for imaging moving organs and to quantify the organ movements.

The present invention provides several methods and systems that relate to the evaluation of an organ motion.

According to the invention, there is provided a method for quantifying a cyclic motion within a series of images depicting a moving object subject to composite motion containing a cyclic component and a non-cyclic component of lower frequency than the cyclic component, the method comprising:

(a) computing the composite motion;
(b) computing the non-cyclic component as the integral of motion over a motion cycle; and
(c) subtracting the non-cyclic component from the composite motion so as to obtain the cyclic component.

The invention provides a novel method of evaluating the cyclic motion of an organ from a series of images of any source and provides implementations of such a method that decrease or eliminate motion artifacts. Specifically, we present a novel method and system for selecting optimal images for the process of 3D reconstruction of the coronaries. We further provide a method and system for replacing the need for ECG Gating by an analysis of the heart movement.

A method for estimating the motion of an organ of a series of images comprises the following operations. A medical imaging device acquires a series of images presenting an organ that is in motion. The motion is either of the organ changing shape (eventually, in a cyclic manner, regaining its original shape) or additionally of the organ changing location within the image (in angiography, for example, it is very common to move the patient's bed while imaging; as a result shifting the coronaries' location within the image). If a non-cyclic component is superimposed on the cyclic motion, the series of images are analyzed to separate the cyclic motion from the non-cyclic motion. Once these two types of motion are separated, the cyclic motion can be quantified. The quantified motion can now be used for direct measurements or can be investigated to identify different events within the motion cycle. In some implementations, this investigation will point to an image that is optimal in the sense that it represents minimal motion and thus yields minimal or no motion artifacts. In other implementations, the cyclic motion investigation will point to several images, on which it is desired to perform an additional procedure or computation. We will specifically present two methods for quantifying the organ's motion.

A preferred embodiment of this invention will include the following. We will present a method and system for identifying the optimal image—(an image depicting minimal coronary movement) from a series of coronary cine-angiograms. We will present a method that separates the heart movement from other movements apparent in the series of angiograms. As a better alternative to the ECG Gating procedure, we suggest to search, using search algorithms such as are known in the art, the graph of the heart motion for the end-diastole position, being the position that represents minimal movement. We correlate this end-diastole position to the appropriate angiogram. This selected angiogram is the optimal image to participate as an input to the procedure of three-dimensional reconstruction of the coronaries. It is optimal in the sense that the 3D model is most representative of the vessels that are imaged. Thus, vessel measurements derived from the model are most accurate.

BRIEF DESCRIPTION OF THE DRAWINGS

In order to understand the invention and to see how it may be carried out in practice, a preferred embodiment will now be described, by way of non-limiting example only, relating to determination of an optimal image within a series of images depicting heart motion, and with reference to the accompanying drawings, in which.

DETAILED DESCRIPTION OF EXEMPLARY EMBODIMENTS

General Principles

The invention will be described with particular reference to the determination of an optimal image within a series of images depicting heart motion possibly containing "noise" caused, for example, by shifting of the operating table on which a patient is disposed. Before doing so, some general algorithms will first be described.

Figure 2:
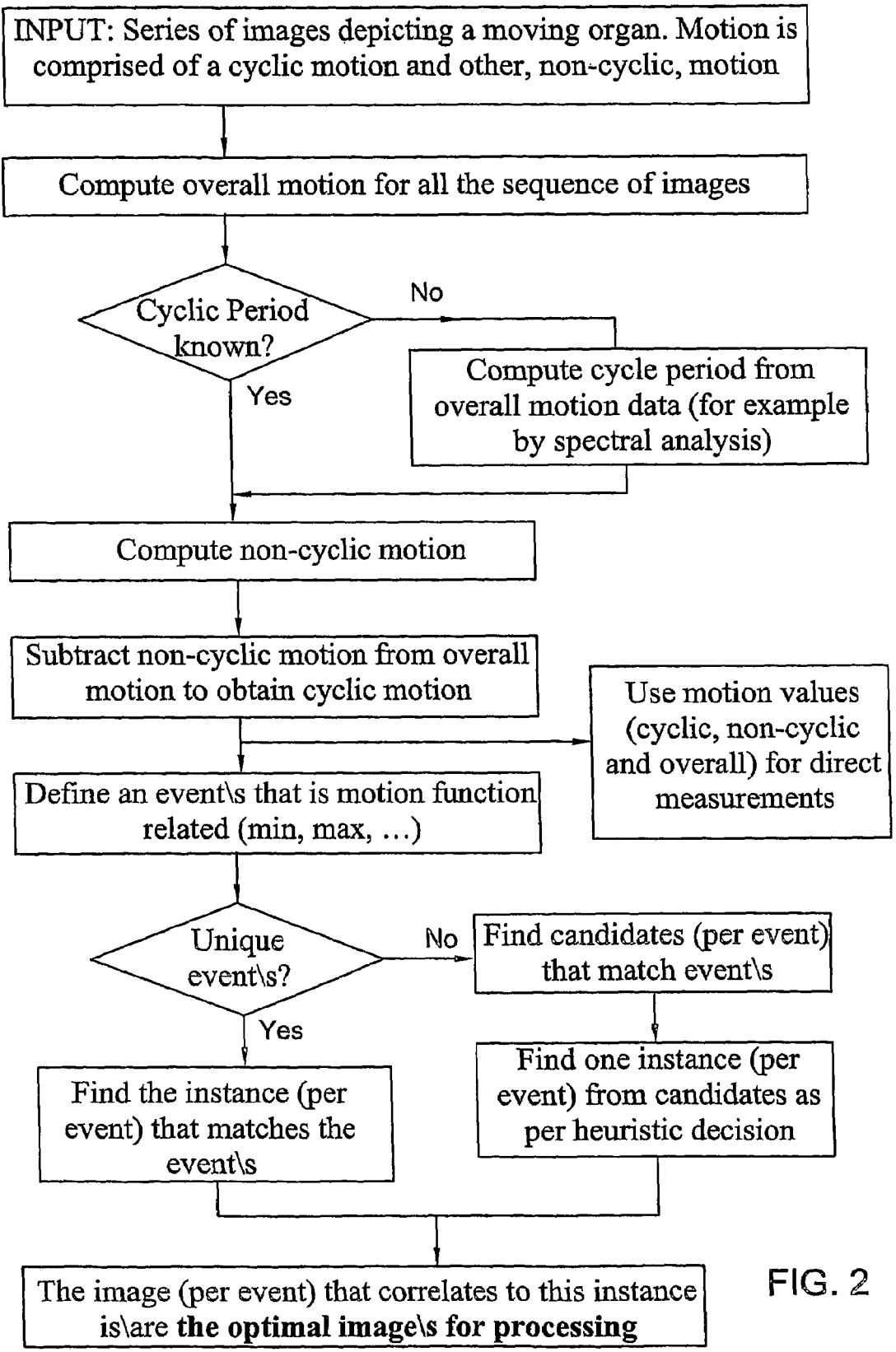
FIG. 2 is a flow chart showing the principal operations carried out in accordance with a general method according to the invention for identifying an optimal image from a series of images depicting a moving object.

FIG. 2 is a flow chart showing the principal operations carried out by a method according to the invention for identifying an optimal image from a series of images that depict a moving object.

Figure 3:
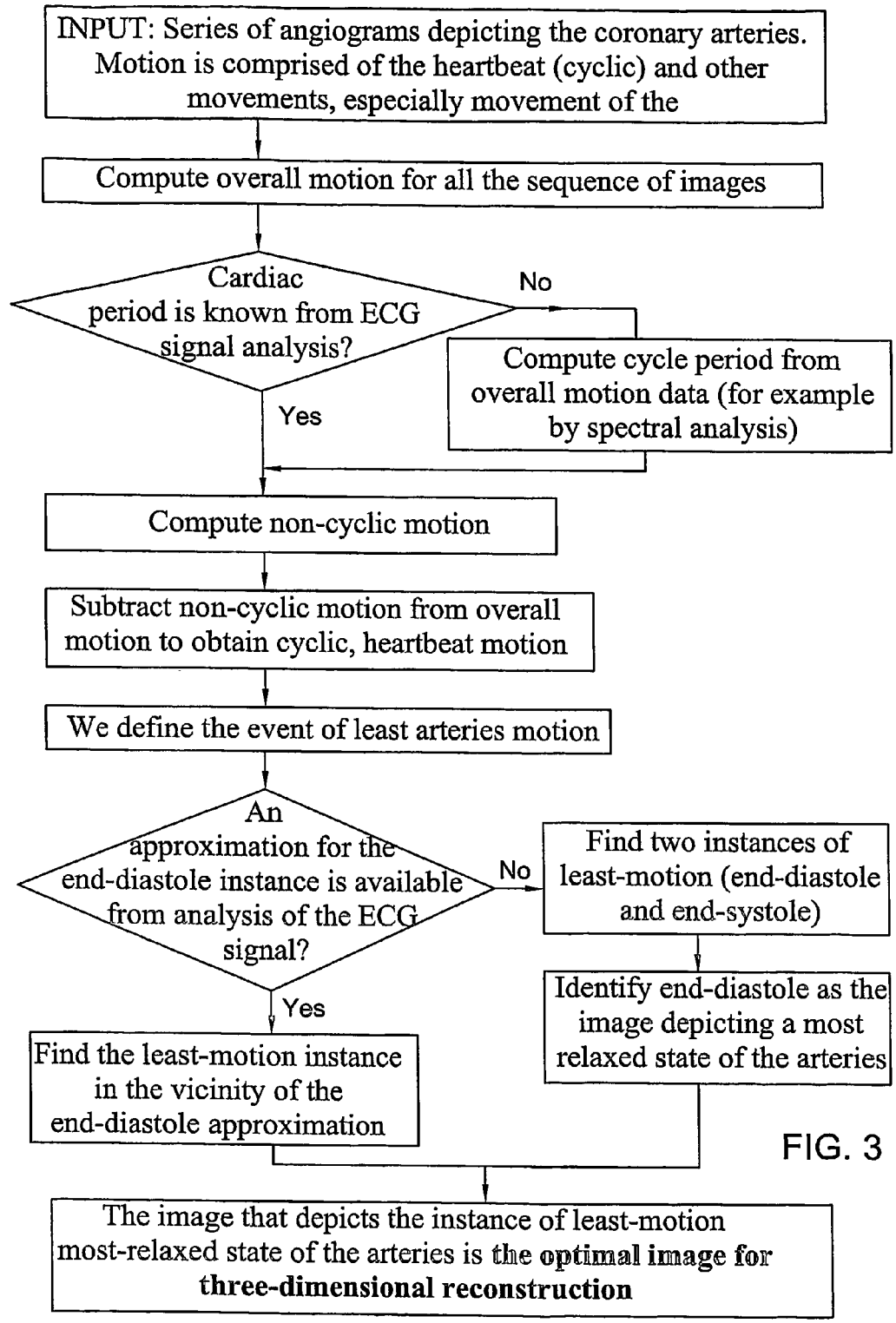
FIG. 3 is a flow chart showing the principal operations carried out in accordance with a specific implementation of the method shown in FIG. 2.

FIG. 3 is a flow chart showing a preferred embodiment of such a method for identifying optimal image from a series of coronary cine-angiography images; this image being the input for a three-dimensional reconstruction of a the coronaries.

A series of images is received as input to from any imaging source. These images depict a moving organ subjected to two types of motions. The first is a cyclic motion of the object itself, meaning that, within a certain time frame, the object restores its original shape and position. The second is the motion of the object within the scene (image), meaning that the object changes position due to change in the imaging position. In the preferred embodiment of this method shown in FIG. 3, the images are a series of coronary angiographic images, obtained during a catheterization procedure. The cyclic motion is the heartbeat and the second motion could be, for example, movement of the C-ARM table, causing a shift of the imaged coronary vessels in the image.

First, the overall motion is computed for all sequence of images, using any method, for example optical flow or phase correlation.

If the cyclic period is unknown, then the cycle period is computed from the overall motion data. One method of doing so is by spectral analysis. The non-cyclic motion is computed, using overall motion and known or computed cycle period. A preferred embodiment of a known cycle period is the period of a cardiac cycle extracted from analysis of the ECG signal.

The non-cyclic motion is subtracted from the overall motion to obtain the cyclic motion. In the preferred embodiment shown in FIG. 3, the heartbeat motion is obtained by subtracting the non-cyclic motion (mainly attributed to movement of the patient's bed) from the overall motion.

The motion values, especially those describing the cyclic motion, can now be used for direct measurements, for example, for cardiac wall motion analysis.

To this end, there is defined an event related to the motion function. For example, in the preferred embodiment shown in FIG. 3, this event could be the minimum instance, identifying the image with least coronary motion, thus being the optimal image for three-dimensional reconstruction.

If the event is unique, then the instance (image) that matches this event is found. Otherwise, all matches for the event are found, and from this list of candidates the one instance that matches a heuristic rule is selected. In the preferred embodiment, the event of least arteries motion could be unique if an approximation to the instance is extracted by analysis of the ECG signal (R peak is an approximation to the end-diastole instance). Otherwise, if such an approximation is not available, the event of least-motion is not unique, since it is matched by both end-systole and end-diastole. Thus, both instances of the least-motion event are found, and the end-diastole motion is identified by the rule that it depicts the arteries most relaxed, as opposed to least relaxed for end-systole motion.

The image that correlates to the identified instance is the optimal image. For example, as in the preferred embodiment, the image that correlates to the event of least-motion, most relaxed state of the arteries is optimal for three-dimensional reconstruction.

Method for Estimating the Organ's Motion

In the above embodiments, motion of the organ is computed from a series of images (frames). Although the manner in which is this is done is not itself a feature of the invention, for the sake of completeness there will now be described ways in which this can be done.

First, we suggest an algorithm, where the number of images (frames) per cyclic motion of the organ is known. This parameter is usually known (for example, the cardiac cycle length is easily acquired via interfacing to the ECG unit in the catheterization room). Nevertheless, we will later obviate the need for knowing this parameter.

Let $IM_1$, $IM_2$ ... $IM_n$ be n images that include, each, an organ that is in cyclic motion. Let m be the number of images per cycle.

Any m+1 images, $IM_1, IM_2 \ldots IM_m, IM_{m+1}$, form a full cycle (for the sake of simplicity it will be assumed that m is an even number). Differences between frames in this sequence are attributed to the organ's cyclic motion, but are also attributed to other factors.

If only cyclic motion is present, the first and the last images in this sequence must be identical, $IM_1 = IM_{m+1}$.

Difference between images representing composite motion can be computed, as known in the art, by, for example, optical flow or by applying phase correlation computation to pairs of successive images $IM_i$ and $IM_{i+1}$, $i \in \{1 \ldots m\}$. The result of this computation (for example the result of phase correlation) is described $dX_i$, $dY_i$ and $\rho_i$, where $dX_i$ and $dY_i$ are the shift between images (assuming a substantial part of the same pattern is present in both images) in X and Y axes respectively and $\rho_i$ is the correlation grade. $\rho_i$ may be used to enhance the further described algorithms.

Let us define and compute the motion integration as:

$$\begin{bmatrix} X_1 \\ Y_1 \end{bmatrix} = \begin{bmatrix} 0 \\ 0 \end{bmatrix}$$

$$\begin{bmatrix} X_{i+1} \\ Y_{i+1} \end{bmatrix} = \begin{bmatrix} X_i \\ Y_i \end{bmatrix} + \begin{bmatrix} dX_i \\ dY_i \end{bmatrix}$$

meaning that in the first image, the motion integral is equal to zero. The motion integral for image i+1 is equal to the motion integral for image i plus shift between images i and i+1, as computed by the phase correlation.

Figure 1:
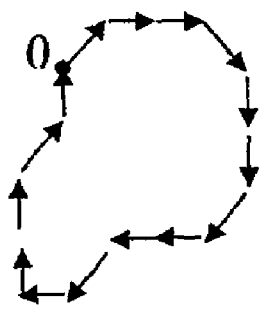
FIG. 1 provides an example that simply demonstrates that the integral of a cyclic motion, being a motion of an object that starts and ends in the same position, is zero.

It is mathematically understandable that the integration of a cyclic motion, from image $IM_1$ to $IM_{m+1}$, is zero—if an object starts and ends in the same position, then the integration of the object movements (on X and Y axis) is zero (as shown in FIG. 1). Thus, if only cyclic motion is present, $(X_{m+1}, Y_{m+1}) = (X_1, Y_1) = (0,0)$.

Let $(X_{NC}, Y_{NC})$ be the integral of the non-cyclic motion, $(X_{NC}, Y_{NC}) = (X_{m+1}, Y_{m+1})$, This means that, given that the integral of cyclic motion is 0, $(X_{m+1}, Y_{m+1})$ represent the residual motion that is attributed to non-cyclic movement.

Assuming non-cyclic motion is consistent, or at the least that its frequency is lower than the cyclic motion frequency, we can subtract this motion from the overall motion:

$(X_i^*, Y_i^*) = (X_i, Y_i) - (X_{NC}, Y_{NC}) * (i-1)/m$, $i = 1, 2, \ldots, m+1$.

Thus, we obtain the following motion values. $(X_{NC}, Y_{NC})$ are the values of the non-cyclic motion, and $(X_i^*, Y_i^*)$, $i = 1, 2, \ldots, m+1$, are the values, per frame i, of the cyclic motion.

These values can now be used for direct measurements (such as cardiac wall motion, for example), and can be used as input to further processing, as further detailed below.

We can obviate the requirement of knowing in advance the length of the cyclic motion by means of direct computation. The most common method of doing so is performing spectral investigation, based on Fast Fourier Transform, applied to a motion graph for the entire sequence, to identify the frequency of the cyclic motion.

Method for Obtaining the Least Motion Image

In many applications, it is desirable to identify the image with least motion (for example, least heart motion or least coronaries motion). In cases where the event of least motion, within the motion cycle is unique, then the least motion image is pointed to by the minimum point on the motion differences graph.

Let:

$$D_{i,j} = \sqrt{(X_i - X_j)^2 + (Y_i - Y_j)^2}$$

$D_{i,j}$ is motion differences graph. Least motion instance is the minimal instance of $D_{i,j}$ function.

In other cases, where the least motion event is not unique within the motion cycle (for example, the cardiac cycle has two least motion instances—end-systole and end-diastole), we suggest the following method.

If an initial approximation for the least motion image is known (for example, the vicinity of the end-diastole image, within the cardiac cycle, is easily identified by the R peak, taken from the ECG signal), then we will find the first extreme point, which is most distant to the approximated least motion image, meaning:

If $IM_F$ is the approximation for the least motion image, then the first extreme point is $D_{E,F} = \max \{D_{i,F}\}$ for all $i = 1 \ldots m+1$.

Least motion image—$IM_{LM}$—is determined as most distant from image $IM_E$, $D_{LM,E} = \max \{D_{i,E}\}$ for all $i = 1 \ldots m+1$.

We can relieve the requirement for knowing in advance an approximation for the least motion image by means of direct computation. If indeed the least motion instance is not unique, we can use heuristic criteria for distinction. For example, within a sequence of angiograms, depicting a cardiac cycle, it is easy to distinguish between the end-systole instance and the end-diastole instance, both representing least motion, since the end-diastole instance is identified by presenting the coronaries in maximal spreading, while the end-systole instance is identified by presenting the coronaries in minimal spreading.

Preferred Embodiment

We suggest a preferred embodiment for an application of three-dimensional reconstruction of coronary vessels from a procedure of conventional angiography. In order to reconstruct a three-dimensional image of the arteries, it is necessary to obtain at least two two-dimensional images of the arteries in the same phase of the heartbeat, for example at end-diastole. Therefore, image acquisition is usually synchronized to an ECG signal. This procedure involves simultaneous recordings of the video signal from the X-ray camera and the patient's ECG signal. We present here a novel method for identifying the end-diastole instance, equivalent to ECG-gating, without relying solely, if at all, on the ECG signal.

Let $IM_1, IM_2 \ldots IM_n$ be n images of a catheterization-acquired run.

Let m be the number of frames per cardiac cycle, either known in advance or computed as detailed in the above-described method for estimating the organ's motion.

Let $IM_k$ be the approximate location of end-diastolic frame within the cycle, either known in advance or heuristically identified as detailed in the above-described method for obtaining the least motion image.

$IM_{k-m/2}, IM_{k-m/2+1}, IM_{k-m/2+1} \ldots IM_{k-m/2+m}$ form a fill cardiac cycle (for the sake of simplicity, let us presume that m is an even number). Differences between frames in this sequence are attributed to heart motion, but are also attributed to bed motion, iodine propagation and several other reasons. If only heart motion were present, the first and the last images in this sequence—$IM_{k-m/2}$ and $IM_{k-m/2+m}$—must be identical, since the motion of the heart is cyclic.

For the sake of simplicity, let us renumber the sequence as $IM_1, IM_2 \ldots IM_m, IM_{m+1}$.

As noted above, if only heart motion is considered then $IM_1=IM_{m+1}$. Also, the end-diastolic renumbered frame is $IM_{m/2+1}$, which is an approximation for the least motion frame.

Apply Phase correlation computation to pairs of successive images $IM_i$ and $IM_{i+1}$, $i \in \{1 \ldots m\}$. The result of the Phase correlation is described $dX_i, dY_i$ and $\rho_i$, where $dX_i$ and $dY_i$ are the shift between images (assuming most of the same pattern—coronary tree or part of the coronary tree—is present in both images) in X and Y axis respectively and $\rho_i$ is the correlation grade. $\rho_i$ may be used to enhance the further described algorithms.

Now, of all the reasons that attribute to the differences between successive images, the most significant contributory factor to such differences—sometimes more than heart motion itself—is bed motion.

Integration of cardiac motion, from image $IM_1$ to $IM_{m+1}$, is zero —$(X_{m+1}, Y_{m+1})=(X_1,Y_1)=(0,0)$.

Let $(X_B, Y_B)$ be the integral of the bed movement, $$(X_B, Y_B) = (X_{m+1}, Y_{m+1}),$$

meaning that, given that the integral of cardiac motion is zero, $(X_{m+1}, Y_{m+1})$ represents the residual motion that is attributed to bed movement.

Assuming the bed movement is consistent (meaning the physician is moving the bed in a general constant direction), or that, as a weaker constraint, the bed movement is slower than heartbeat, we can subtract this movement from the overall movement:

$$(X_i^*, Y_i^*) = (X_i, Y_i) - (X_B, Y_B)*(i-1)/m, i=1, 2, \ldots, m+1.$$

The frame with minimum arterial motion is pointed by the extreme point on (X,Y) curve.

Let:

$$D_{i,j} = \sqrt{(X_i-X_j)^2+(Y_i-Y_j)^2}$$

We can determine the end-systole point S, which is the one most distant from the approximated end-diastole point, meaning:

$$D_{S,m/2+1} = \max \{D_{i,m/2+1}\}$$

Minimum motion point—end-diastole, ED—is determined as most distant from systole point:

$$D_{S,ED} = \max \{D_{S,j}\}.$$

Selecting the $IM_{ED}$ image per sequence of cine-angio images for the process of three-dimensional reconstruction will provide the optimal result, in terms of accuracy and precision, for the reconstruction and for vessel analysis.

In the method claims that follow, alphabetic characters and Roman numerals used to designate claim steps are provided for convenience only and do not imply any particular order of performing the steps.

It will also be understood that the system according to the invention may be a suitably programmed computer. Likewise, the invention contemplates a computer program being readable by a computer for executing the method of the invention. The invention further contemplates a machine-readable memory tangibly embodying a program of instructions executable by the machine for executing the method of the invention.

The invention claimed is:

1. A method for obtaining a cyclic motion within a series of images depicting a moving object subject to composite motion containing a cyclic motion component having a cyclic period and a non-cyclic consistent component of a lower frequency than the cyclic motion component, the method comprising: a computer performing the steps of:
    (a) computing the composite motion between at least one pair of successive images, the composite motion represented by at least one vector;
    (b) computing the non-cyclic consistent component as an integral of the composite motion over the cyclic period;
    (c) computing a proportional part of the non cyclic consistent component for each of the at least one pair of successive images; and
    (d) for each of the at least one pair of successive images, subtracting the proportional part of the non-cyclic consistent component from the composite motion so as to obtain the cyclic motion component,
    wherein the series of images comprises an at least one series of N images acquired during a cyclic period, each frame having an index i within the cyclic period, i=1 . . . N, and wherein the proportional part of the non cyclic component for each of the at least one pair of successive images i-1 and i is determined by dividing the non cyclic component by N and multiplying by i-1.

2. The method according to claim 1, wherein the cyclic period of the cyclic motion component is computed using spectral analysis.

3. The method according to claim 1, wherein the composite motion is determined by optical flow.

4. The method according to claim 1, wherein the composite motion is determined using phase correlation of said images.

5. The method according to claim 1, where cyclic motion values are used for evaluating performance of a body organ.

6. The method according to claim 4, when used in a cardiac application to evaluate heart performance.

7. The method according to claim 6, when used for Ejection Fraction analysis.

8. The method according to claim 6, when used for Left Ventricular analysis.

9. The method according to claim 6, when used for Wall Motion analysis.

10. A method for identifying an image depicting an event associated with cyclic motion, the method comprising:
    (a) computing the cyclic motion according to the method of claim 1;
    (b) using a graphical representation of the cyclic motion to identify all images matching said event; and
    (c) selecting one of said images.

11. The method according to claim 10, wherein the selected image is closest to a predetermined approximation.

12. The method according to claim 10, wherein the event is least motion.

13. The method according to claim 12, for selecting angiographic images to participate in three-dimensional reconstruction of coronary vessels.

14. The method according to claim 13, including deriving cycle period and approximation for least-motion image from an analysis of an electro cardiogram (ECG) signal.

15. The method according to claim 13, including distinguishing the end diastole instance from the end-systole instance by the state of coronary vessel—maximal spreading versus minimal spreading, respectively.

16. The method according to any one of claim 1 when used for selecting optimal image or images for Quantitative Coronary (QCA) analysis.

17. The method according to any one of claim 1 when used for selecting optimal image or images for Intra Vascular Ultra Sound (IVUS) analysis.

18. The method according to any one of claim 1 when used for selecting optimal image or images for Left Ventricular LVA) analysis.

19. The method according to claim 1 when used for selecting optimal image or images for Wall Motion analysis.

20. The method according to any one of claim 1 when used for Computerized Tomography (CT)reconstruction.

21. The method according to any one of claim 1 when used for Magnetic Resonance Imaging (MRI) reconstruction.

22. The method according to any one of claim 1 when used for Positron Emission Tomography (PET) reconstruction.

23. A system for obtaining a cyclic motion within a series of images depicting a moving object subject to composite motion containing a cyclic motion component having a cyclic period and a non-cyclic consistent component of a lower frequency than the cyclic motion component, the system comprising:
   a composite motion unit for computing the composite motion between at least one pair of successive images, the composite motion represented by at least one vector;
   a non-cyclic motion unit for computing the non-cyclic consistent component as an integral of the composite motion over the cyclic period;
   a proportional part unit for computing a proportional part of the non cyclic motion component for each of the at least one pair of successive images; and
   a subtraction unit for subtracting the proportional part of the non-cyclic consistent component from the composite motion occurring between each of the at least one pair of successive images, so as to obtain the cyclic motion component,
   wherein the series of images comprises an at least one series of N images acquired during a cyclic period, each frame having an index i within the cyclic period, i=1 . . . N, and wherein the proportional part of the non cyclic component for each of the at least one pair of successive images i-1 and i is determined by dividing the non cyclic component by N and multiplying by i-1 , wherein at least one of the above units is implemented in a hardware or hardware software combination.

24. A system for identifying an image depicting an event associated with cyclic motion, the system comprising:
   the cyclic motion system of claim 23 for computing the cyclic motion and deriving data representative of a graphical representation thereof,
   an image identification unit responsive to said data representative of a graphical representation of the cyclic motion for identifying all images matching said event, and
   an image selection unit for selecting one of said images.

25. The system according to claim 24, wherein the image identification unit is adapted to identify minimal cyclic motion.

26. The system according to claim 25, wherein the image selection unit is adapted to select angiographic images to participate in three-dimensional reconstruction of coronary vessels.

27. The system according to claim 26, including an Electro Cardiogram (ECG) analyzer for deriving cycle period and approximation for least-motion image from an analysis of an ECG signal.

28. The system according to claim 26, including an image processing unit coupled to the image selection unit for distinguishing the end-diastole instance from the end-systole instance by the state of coronary vessel—maximal spreading versus minimal spreading, respectively.

* * * * *